(12) United States Patent
Burnie et al.

(10) Patent No.: US 6,881,410 B2
(45) Date of Patent: Apr. 19, 2005

(54) **TREATMENT OF *E. FAECIUM* INFECTION**

(75) Inventors: James Peter Burnie, Alderley Edge (GB); Ruth Christine Matthews, Alderley Edge (GB)

(73) Assignee: Neu Tec Pharma PLC, Manchester (GB)

( * ) Notice: Subject to any disclaimer, the term of this patent is extended or adjusted under 35 U.S.C. 154(b) by 143 days.

(21) Appl. No.: 10/054,968

(22) Filed: Jan. 25, 2002

(65) Prior Publication Data

US 2003/0119101 A1 Jun. 26, 2003

Related U.S. Application Data

(62) Division of application No. 09/214,307, filed as application No. PCT/GB97/01830 on Jul. 7, 1997, now Pat. No. 6,544,516.

(30) Foreign Application Priority Data

Jul. 6, 1996 (GB) .............................................. 9614274

(51) Int. Cl.$^7$ ................................................ A61K 39/40
(52) U.S. Cl. ................ 424/150.1; 424/93.2; 424/163.1; 424/164.1; 424/234.1; 530/388.4; 530/389.5
(58) Field of Search ............................ 424/93.2, 150.1, 424/163.1, 164.1, 234.1; 435/732; 530/388.4, 389.5, 825

(56) References Cited

U.S. PATENT DOCUMENTS 5,747,239 A 5/1998 Wang et al.

FOREIGN PATENT DOCUMENTS

WO WO 93/06247 4/1993
WO WO 95/20658 8/1995

OTHER PUBLICATIONS

Ristori et al. Compositional bias and mimicry toward the nonself proteome in immunodominant T cell epitopes of self and nonself antigens. FASEB Journal (2000) vol. 14, No. 3, pp. 431–438.*
Casadevall et al. Return to the Past: The case for antibody-based therapies in infectious diseases. Clinical Infectious Diseases (1995) vol. 21, pp. 150–161.*
Paul W.E.(Fundamental Immunology, Raven Press, New York, NY; (1993) 3rd Edition, p. 249, 251.*
Klein Self–nonself discrimination, histoincompatibility, and the concept of immunology. Immunogenetics (1999) vol. 50, No. 3–4, pp. 116–123.*
I.M. Clark et al., "Isolation and sequence determination of an immunodominant antigen from *enterococcus faecalis*" Serodiagnosis & Immunotherapy in Infectious Disease, vol. 5, No. 2, Jul. 1993, pp. 85–92.

A. Sulaiman et al., "Serological investigation of enterococcal infections using western blot" European Journal of Clinical Microbiology & Infectious Diseases, vol. 5, No. 10, Oct. 1996, pp. 826–829.
M.J. Fath et al., "ABC Transporters bacterial exporters" Microbiological Reviews, vol. 57, No. 4, Dec. 1993, pp. 995–1017.
M. Frosch et al., "Conserved outer membrane protein of neisseria meningitidis involved in capsule expression" Infection and Immunity, vol. 60, No. 3, Mar. 1992, pp. 798–803.
M. Frosch et al. "Evidence for a common molecular origin of the capsule gene loci in Gram–negative bacteria expressing group II capsular *polysaccharides*." Molecular Microbiology, vol. 5, No. 5, 1991, pp. 1251–1263.
Gillmore et al. "An HlyB–type function is required for expression of the *Enterococcus faecalis* hemolysisn/bacteriocin." Infection and Immunity. vol. 58, No. 12, 1990, pp. 3914–3923.
Weisman et al. "Intravenous immune globulin prophylaxis of late–onset sepsis in premature neonates." Journal of Pediatrics, vol. 124, 1994, pp. 922–930.
J. Klein, "Self–nonself discrimination, histocompatibility, and the concept of immunology." Immunogenetics, vol. 50, 1999, pp. 116–123.
W. Paul. "Fundamental Immunology." Raven Press, ltd. New York, NY, 1993, pp. 249–251.
Ristori et al. "Compositional bias and mimicry toward the nonself proteome in immunodominant T cell epitopes of self and nonself antigens." FASEB Journal, vol. 14, 2001, pp. 431–438.
A. Casadevall et al. "Return to the past: the case for antibody–based therapies in infectious diseases." Clinical Infectious Diseases, vol. 21, 1995, pp. 150–161.

* cited by examiner

Primary Examiner—James Housel
Assistant Examiner—Ulrike Winkler
(74) Attorney, Agent, or Firm—Mayer Brown Rowe & Maw LLP

(57) ABSTRACT

The present invention provides bacterial and fungal ABC transporter proteins, immunogenic fragments thereof, neutralising agents specific thereto and binding agents specific thereto for therapeutic and diagnostic use, together with diagnostic test methods, methods of same and kits for performing same. Also provided are immunodominant conserved antigens from gram positive staphylococci, together with neutralising and binding agents specific thereto for use in therapy and diagnosis, and methods of same. Also provided are Staphylococcal holomogues of IstA and IstB and immunogenic fragments thereof, and their uses in methods of treatment and diagnosis of the human or animal body.

10 Claims, 3 Drawing Sheets

TREATMENT OF E. FAECIUM INFECTION

CROSS REFERENCE TO RELATED APPLICATIONS

Figure 1:
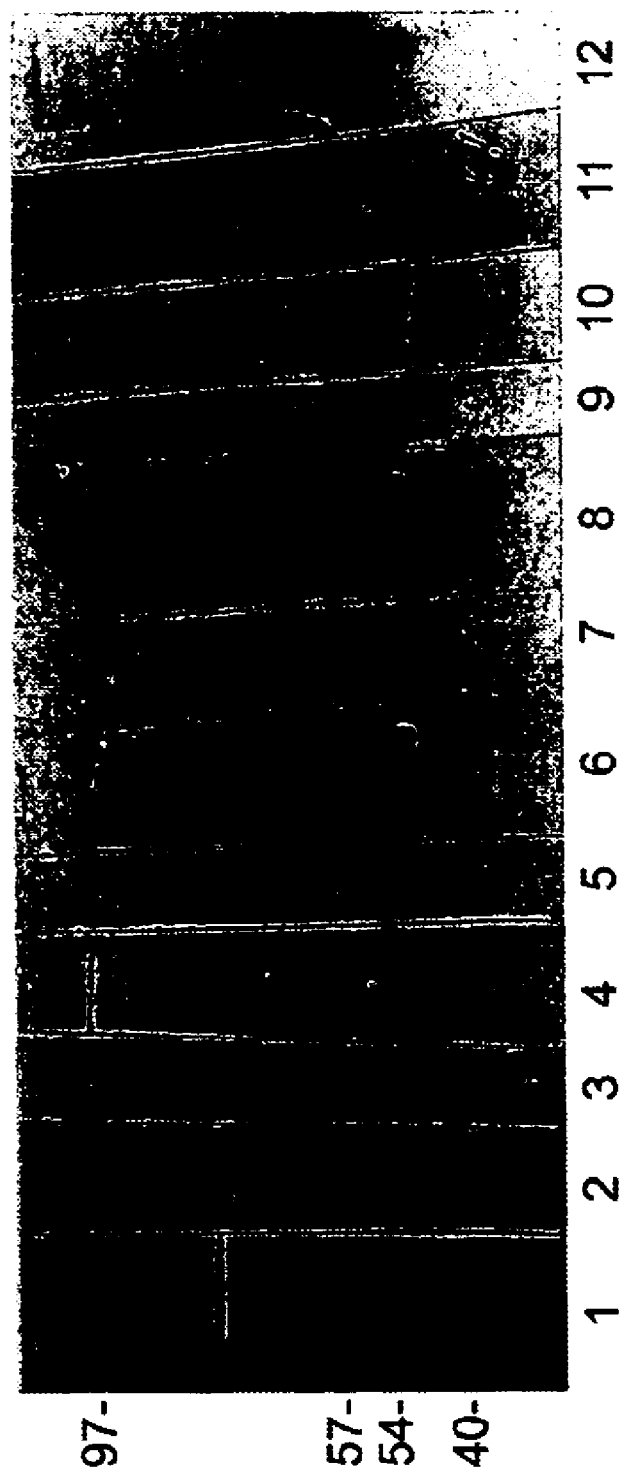

This application is a divisional of U.S. Ser. No. 09/214,307, filed Jan. 4, 1999 now U.S. Pat. No. 6,544,516, which is a national phase application based on PCT/GB97/01830, filed Jul. 7, 1997, and which further claims priority from British Application No. 9614274.0, filed Jul. 6, 1996. These applications are incorporated herein by reference.

The present invention concerns the treatment and diagnosis of infections of bacteria and fungi, particularly of gram positive cocci, in particular enterococci and staphylococci.

The widespread use of antibiotics and other agents (for example penicillin vancomycin, methicillin, cephalosporin, tetracycline, chloramphenicol, glycopeptides and aminoglycosides) to treat bacterial infections has led to the rapid development of bacteria resistant to the agents (see for example CDC, 1993, JAMA, 270: 1796; IDCP, 1996, Infect Dis. Clin Pract., 5: 1–2; Spera, R. V. and Farber, B. F., 1994, Drugs, 48: 678–688) and many bacteria have multiple drug resistance. This proves a particular problem in clinical environments (Morris, J. G. et al., 1995, Ann. Intern. Med., 123: 250–259; Boyce, J. M. et al., 1994, J. Clin. Micro., 32: 1148–1153). Bacteria which are particularly problematic are Enterococci and Staphylococci.

Enterococci are the second most common hospital-acquired infections in the USA, causing intra-abdominal abcesses, endocarditis, infections of the urinary tract and soft tissues and septicaemia (with a high morality of 34–68%). They are now resistant to ampicillin, gentamicin and, increasingly, vancomycin. VRE (vancomycin-resistant enterococci) are currently untreatable and are responsible for 14% of sepsis in intensive care units. There has been a 20 fold increase in VRE between 1989 and 1993 (CDC National Nosocomial Infection Surveillance; WHO Report, 1996).

*Staphylococcccus aureus* is one of the commonest causes of skin infection, septicaemia, osteomyelitis and endocarditis. 26% of *S. aureus* isolates in France (1989), and in the USA (1991) 38.3%, were multi-resistant MRSA (methicillin resistant *S. aureus*). The MRSA is resistant to all antibiotics except vancomycin and morality from MRSA septicaemia is 40%. However, the use of vancomycin is one of last resort since it may cause nephrotoxicity, ototoxicity, bone marrow toxicity and the red man syndrome. Transfer of vancomycin-resistance from a VRE to *S. aureus* has been demonstrated in the laboratory and clinically with certain species of staphylococcus. There is a significant possibility that this may occur with *S. aureus* in patients, and would lead to the creation of a bacterium untreatable by current therapies.

According to the present invention there is provided a bacterial or fungal ABC transporter protein or an immunogenic fragment thereof for use in a method of treatment of the human or animal body. There is also provided a bacterial or fungal ABC transporter protein or an immunogenic fragment thereof used in the manufacture of a medicament.

ABC transporters are well known (Faith, M. J. and Kolter, R., 1993, Microbiological Reviews, 57(4): 995–1017; Borenkamp, S. J. and St Geme, J. W. III, 1994, Infection and Immunity 62: 3320–3328). However, they have no known therapeutic application, nor has one been suggested. Similarly, agents which neutralise their activity have not been proposed for a therapeutic application.

Particular uses of the ABC transporter protein or immunogenic fragment include their use as immunogens, for example as vaccines.

Reference to ABC transporter proteins is to both importer and exporter proteins. Reference to immunogenic fragment is also reference to analogues of immunogenic fragments, particularly mimotopes (Geysen H. M. et al, 1987, Journal of Immunological Methods, 102:259–274; Geysen, H. M. et al., 1988, J. Mol. Recognit, 1(1):32–41).

A bacterium may be an enterccoccus, for example selected from the group of *E.faecium, E.faecalis, E.avium, E.gallinarium, E.durans, E.mundtii* and *E.casseflavus*.

The experimental section (below) describes particular enteroccal ABC transporter proteins having weights of 97 and 54 kDa. Hence the ABC transporter protein may be an enteroccal protein selected from the group of 97 and 54 kDa immunodominant conserved antigens.

The 97 and 54 kDa enteroccal immunodominant conserved antigens are not novel per se (Clark, I. M. and Burnie, J. P., 1993, Serodiagn. Immunother. Infect Disease, 5: 85–92; Sulaiman, A. et al., 1996, Eur. J. Clin. Microbiol Infect Dis., 15:826–829). However, they have not been previously identified or suggested as being ABC transporter proteins, nor have they been suggested for a therapeutic application, nor have agents which neutralise them.

An immunogenic fragment may comprise an ATP binding site or a part thereof. Specific (therapeutically useful) epitopes have been determined to be displayed by the ATP binding sites of ABC transporters, and so they or neutralising agents specific to them may be used therapeutically. Similarly, agents which bind to them may be used diagnostically.

An enteroccal immunogenic fragment may have the sequence of SEQ ID NO: 3, and is displayed by the ABC transporters of e.g. *E.faecium* and F.faecalis.

An E.faeciumimmunogenic fragment may have the sequence of SEQ ID NO: 4.

A number of *E.faecium* specific epitopes have been found, and so the immunogenic fragment may have the sequence of any one of SEQ ID NOs: 5–8.

Also provided according to the present invention are neutralising agents specific to a bacterial or fungal ABC transporter protein or immunogenic fragment thereof for use in a method of treatment of the human or animal body.

A neutralising agent may be used in the manufacture of a medicament.

Neutralising agents are well known and may include antibodies and antigen binding fragments thereof (Harlow, E. and Lane, D., "Antibodies—A Laboratory Mannual", Cold Spring Harbor Laboratory, Cold Spring Harbor Press, New York, 1988), ribozymes and antisense nucleic acid chains. Other neutralising agents will be readily apparent to one skilled in the art.

Also provided according to the present invention is a method of treatment of the human or animal body comprising treating a patient with a bacterial or fungal ABC transporter protein or an immunogenic fragment thereof or a neutralising agent specific thereto according to the present invention.

Medicaments according to the present invention may additionally comprise a pharmaceutically acceptable carrier, diluent or excipient (Remington's Pharmaceutical Sciences and US Pharmacopea, 1984, Mack Publishing Company, Easton, Pa., USA).

Also provided according to the present invention is a bacterial or fungal ABC transporter protein or an immunogenic fragment thereof for use in a method of diagnosis of the human or animal body. The ABC transporter or immunogenic fragment thereof may be used in a method of diagnosis.

The bacterium may be an enterococcus, for example selected from the group of *E.faecium, E.faecalis, E.avium, E.gallinarium, E.durans, E.mundtii* and *E.casseflavus*.

The ABC transporter protein may be an enterocccal protein selected from the group of 97 and 54 kDa immunodominant conserved antigens.

An immunogenic fragment may comprise an ATP binding site or a part thereof.

The bacterium may be an enterocous, the immunogenic fragment having the sequence of SEQ ID NO: 3. The bacterium may be E.faecium, the immunogenic fragment having the sequence of SEQ ID NO: 4

The bacterium may be E.faecium, the immunogenic fragment having the sequence of any one of SEQ ID NOs: 5–8.

Also provided according to the present invention is a binding agent specific to a bacterial or fungal ABC transporter protein or immunogenic fragment thereof according to the present invention for use in a method of diagnosis of the human or animal body.

Also provided according to the present invention is a binding agent specific to a bacterial or fungal ABC transporter protein or immunogenic fragment thereof according to the present invention used in a method of diagnosis.

Also provided according to the present invention is a binding agent according to the present invention used in the manufacture of a diagnostic test kit.

Binding agents include any agent capable of detecting the protein or immunogenic fragment and are well known, and include, for example, antibodies and antigen binding fragments thereof.

Also provided according to the present invention is a method of diagnosis of the human or animal body comprising the use of a bacterial or fungal ABC transporter or an immunogenic fragment thereof or a binding agent specific thereto according to the present invention.

Also provided is a diagnostic test method for a bacterial or fungal ABC transporter protein or an immunogenic fragment thereof according to the present invention comprising the steps of:
i) reacting a binding agent according to the present invention with a sample from a patient;
ii) detecting a reaction between the binding agent and antigen; and
iii) correlating the detection of the reaction with the presence of the protein or an immunogenic fragment thereof.

A sample from a patient may for example be patient dialysate or serum.

The binding agent may comprise an antibody, the diagnostic test method comprising the steps of:
i) reacting an antibody according to the present invention with a sample from a patient;
ii) detecting an antibody-antigen binding reaction; and
iii) correlating the detection of the antibody-antigen binding reaction with the presence of the protein or an immunogenic fragment thereof.

Also provided is a diagnostic test method for antibody specific against a bacterial or fungal ABC transporter protein or an immunogenic fragment thereof according to the present invention comprising the steps of:
i) reacting an ABC transporter protein or an immunogenic fragment thereof according to the present invention with patient antisera;
ii) detecting an antibody-antigen binding reaction; and
iii) correlating the detection of the antibody-antigen binding reaction with the presence of antibody specific against the bacterial or fungal ABC transporter or an immunogenic fragment thereof.

Also provided is a kit of parts for performing a diagnostic test according to the present invention.

Also provided is a method of diagnosis comprising the use of a bacterial or fungal ABC transporter protein or an immunogenic fragment thereof or a binding agent specific thereto according to the present invention.

Also provided according to the present invention is a Staphylococcal homologue of IstA or IstB or an immunogenic fragment thereof. The staphylococcus may for example be S. aureus, coagulase negative staphylococci, S. epidermidis; S. haemolyticus or S. hyicus.

The homologues have been found to be 69 and 37 kDa immunodominant conserved antigens. By immunodominant conserved antigen is meant an antigen which elicits an immunogenic response in at least 50% of infected patients.

The Staphylococcus may be S.aureus, the homologue being of IstA and having the sequence of SEQ ID NO: 10, or an immunogenic fragment thereof. An immunogenic fragment of a S.aureus homologue of IstA may have the sequence of any one of SEQ ID NOs: 12–14.

The Staphylococcus may be S.aureus, the homologue being of IstB and having the sequence of SEQ ID NO: 11, or an immunogenic fragment thereof. An immunogenic fragment of a S.aureus homologue of IstB may have the sequence of SEQ ID NO: 15.

Also provided is a neutralising agent specific against a Staphylococcal homologue of IstA or IstB or an immunogenic fragment thereof according to the present invention.

Also provided is a binding agent specific to a Staphylococcal homologue of IstA or IstB or an immunogenic fragment thereof according to the present invention.

A Staphylococcal homologue of IstA or IstB or an immunogenic fragment thereof, or a neutralising agent specific thereto or a binding agent specific thereto according to the present invention may be for use in a method of treatment or diagnosis of the human or animal body.

A Staphylococcal homologue of IstA or IstB or an immunogenic fragment thereof, or a neutralising agent specific thereto or a binding agent specific thereto according to the present invention may be used in a method of treatment or diagnosis.

Also provided is a method of treatment or diagnosis of the human or animal body comprising the use of a Staphylococcal homologue of IstA or IstB or an immunogenic fragment thereof, or a neutralising agent specific thereto or a binding agent specific thereto according to the present invention.

The present inventors have now succeeded in isolating two immunodominant conserved enterococcal antigens and two immunodominant conserved staphylococcal antigens and have found that, surprisingly, antibody specific to these antigens may be used to provide an effective therapy for enterococcal and staphylococcal infection.

The antigen may be for use in a method of treatment or diagnosis of the human or animal body.

The antigen may be for use as an immunogen. Hence the antigen may be used to stimulate an immunogenic response in patients in order to protect them against infection from the bacteria. The antigen may for example be for use as a vaccine.

The present invention also provides antibody or an antigen binding fragment thereof specific to an antigen according to the present invention. The antibody or an antigen binding fragment thereof may be for use in the diagnosis or treatment of infections of the enterococcus or staphylococcus. In the case of bacteria having multiple drug resistance, in particular those for which there is no current drug therapy, the use of antibody specific to the bacteria provides a novel and highly effective form of treatment for the infection.

The role that antibodies play in enterococcal and staphylococcal infection has not yet been fully defined (Moellering, R. C., 1995, In: Mandell, G. L., Bennett, J. E. and Dolin, R (eds.), Mandell, Douglas and Bennett's Principles and Practice of Infectious Diseases, Fourth Edn., Churchill Livingstone, 1826–1835). Aitchison, E. J. et al. (1986, J. Med. Microbiol., 21: 161–167) investigated the surface components of an endocarditis associated isolate of *E.faecalis* using SDS-PAGE (sodium dodecyl sulphate polyacrylamide gel electrophoresis) and Western blotting. A major envelope protein antigen of molecular weight 53 kDa was defined in *E. faecalis* (and not in *E. faecium*). and other common antigens of *E. faecalis* had molecular weights of 65, 63, 56, 49.5. 30 and 21 kDa. They also found that growth of *E. faecalis* in serum to mimic in vivo growth conditions in endocarditis patients altered the antigenic pattern, with only two major antigens of molecular weights 56 and 53 kDa reacting with sera from endocarditis patients. They suggested that these antigens may be of diagnostic potential. Burnie, J. P. et al. (1987, J. Clin. Pathol., 40: 1149–1158) explored the role of immunoblotting in the diagnosis of culture-negative and enterococcal endocarditis. They found that in *E. faecalis* endocarditis there was a strong IgM response to *E.faecalis* bands of 112, 88–90 and 45–47 kDa, and a strong IgG response to 88–90 and 45–47 kDa bands. The 112 kDa antigen of *E. faecalis* was later used to develop an indirect enzyme-linked immmunosorbent assay (ELISA) for the diagnosis of *E.faecalis* endocarditis (Burnie, J. P. and Clark, I., 1989, J. Immunol. Methods, 123: 217–225). The three patients with *E. faecium* infection showing a strong IgG response to bands of 82–90 kDa.

The antibody may be a whole antibody or an antigen binding fragment thereof and may in general belong to any immunoglobulin class. Thus, for example, it may be an immunoglobulin M antibody or an immunoglobulin G antibody. The antibody or fragment may be of animal, for example, mammalian origin and may be for example of murine, rat, sheep or human origin. It may be a natural antibody or a fragment thereof, or, if desired, a recombinant antibody fragment i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in, for example, European Patent Specification No 239400); (2) recombinant antibodies or fragments wherein non-Fv sequences have been substituted by non-Fv sequences from other, different antibodies (as described in, for example, European Patent Specification Nos 171469, 173494 and 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, International Patent Application Nos PCT/GB88/00730 and PCT/GB88/00729).

The antibody or antibody fragment may be of polyclonal, monoclonal or recombinant origin. It may be specific for at least one epitope.

Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described, for example, in International Patent Application No PCT/GB8810747).

The antibodies according to the invention may be prepared using well-known immunological techniques employing the protein expressed during infection as antigen. Thus, for example, any suitable host may be injected with the protein and the serum collected to yield the desired polyclonal antibody after appropriate purification and/or concentration (for example by affinity chromatography using the immobilised protein as the affinity medium). Alternatively splenocytes or lymphocytes may be recovered from the protein injected host and immortalised using for example the method of Kohler et al. (1976, Eur. J. Immunol., 6: 511), the resulting cells being segregated to obtain a single genetic line producing monoclonal antibodies. Antibody fragments may be produced using conventional techniques, for example, by enzymatic digestion with pepsin or papain. Where it is desired to produce recombinant antibodies according to the invention these may be produced using, for example, the methods described in European Patent Specification Nos 171469, 173494, 194276 and 239400.

Antibodies according to the invention may be labelled with a detectable label or may be conjugated with an effector molecule, for example a drug e.g. an antibacterial agent or a toxin or an enzyme, using conventional procedures and the invention extends to such labelled antibodies or antibody conjugates.

Such antibody may for example be expressed in transgenic animals, for example transgenic sheep and may be achieved using existing transgenic expression systems.

According to the present invention there is also provided methods of treatment and diagnosis of infections due to streptococci and enterococci comprising the use of an immunodominant conserved antigen according to the present invention or an antibody specific thereto or an antigen binding fragment thereof.

The invention will be further apparent from the following description, with reference to the several figures of the accompanying photographs which show by way of example only immunoblots of patients infected and colonized with VRE.

Figure 2:
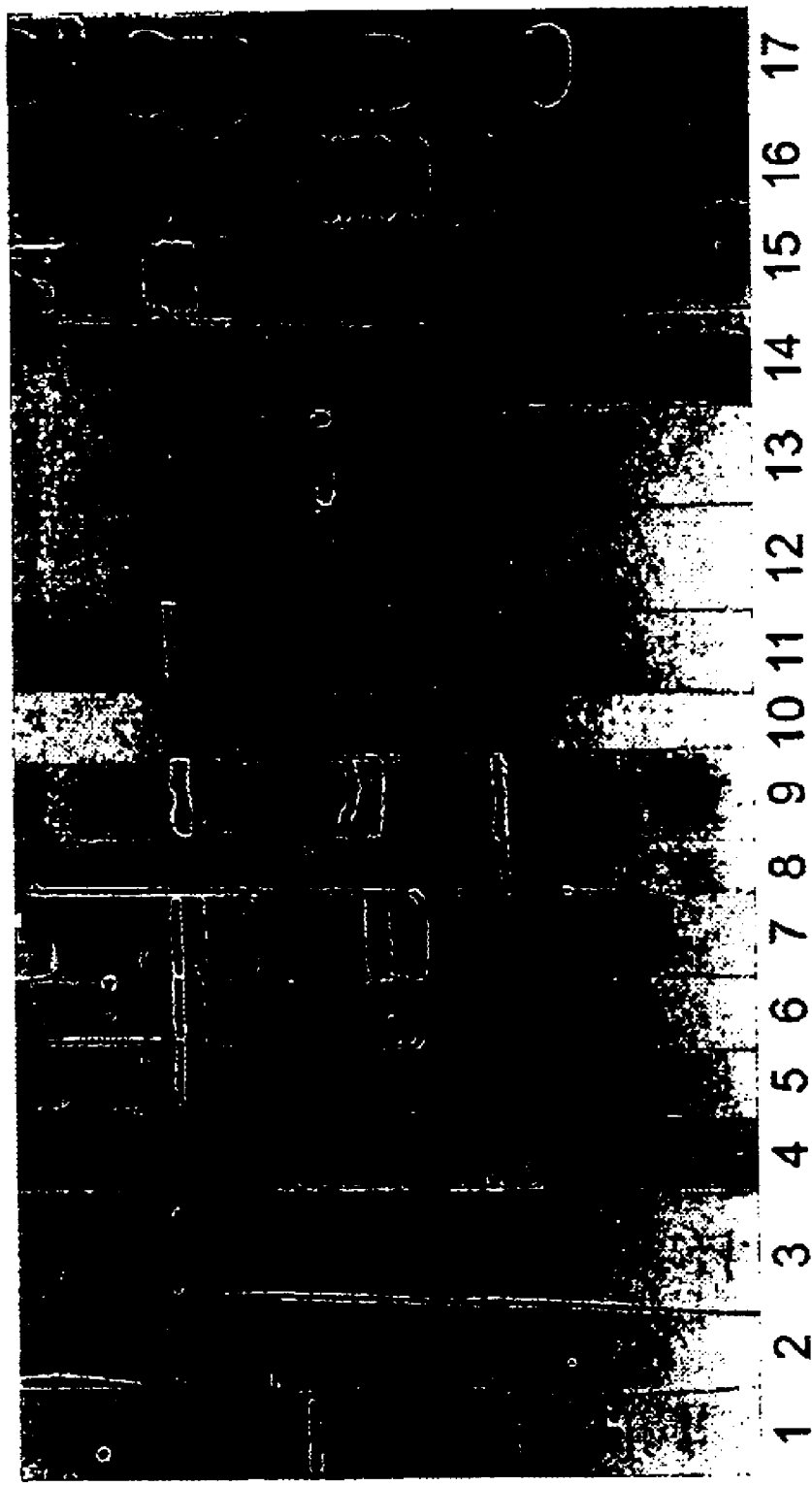
Figure 3:
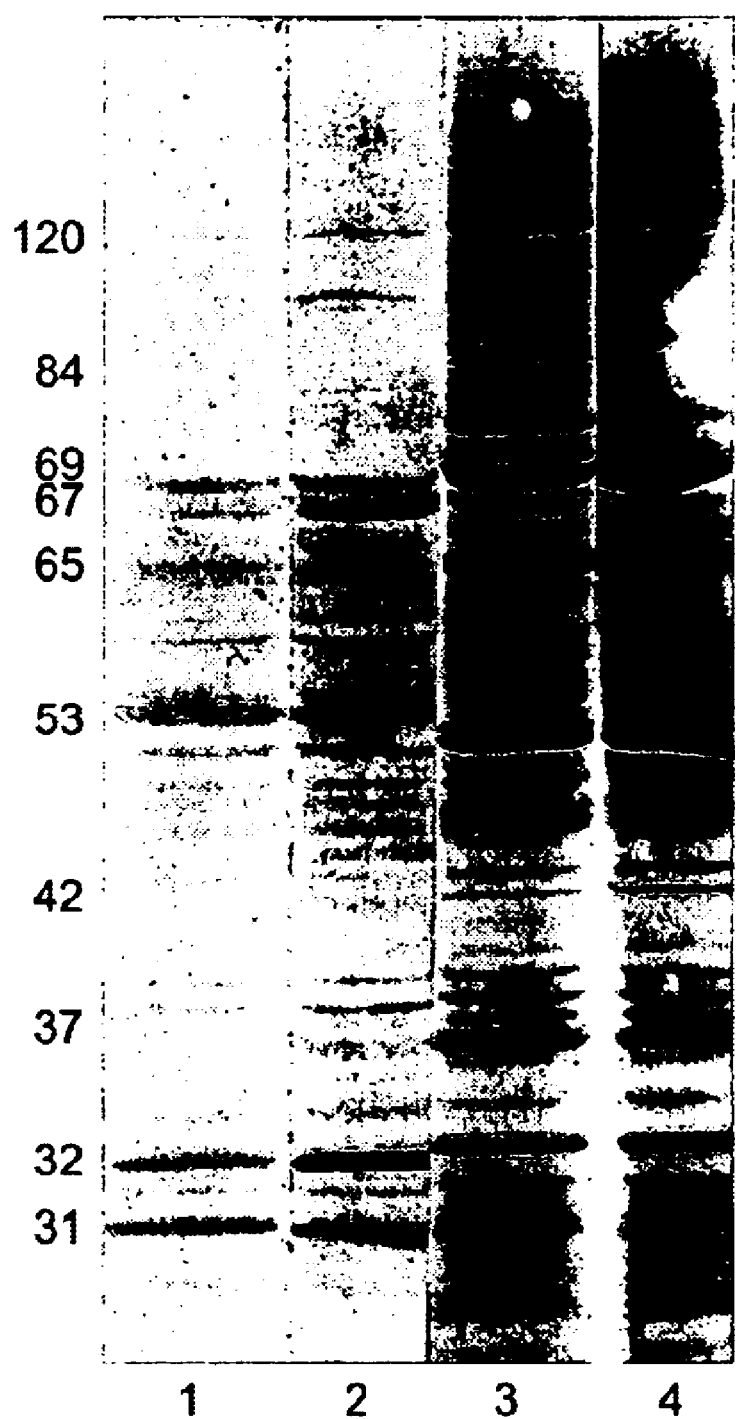

Of the figures:

FIG. 1 shows pre- and post- VRE infection immunoblots for the IgM response of five patients (lanes 1 and 2, 3 and 4, 5 and 6, 7 and 8, 9 and 10 respectively). Lane 11 is a post-VRE infection immunoblot for the IgM response of one patient. All patients had a septicaemia (Table 2);

FIG. 2 shows the IgG response of pre- and post- VRE infection patients. Lanes 1–15 are post-infection from all ten replicants and the pre-infection from five of the replicants (Table 2). Lanes are: 1 (post, patient 1), 2 (post, patient 2), 3 (post, patient 3), 4 (pre, patient 4), 5 (post, patient 4), 6 (pre, patient 5), 7 (post, patient 5), 8 (pre, patient 6), 9 (post, patient 6), 10 (pre, patient 7), 11 (post, patient 7), 12 (pre, patient 8), 13 (post, patient 8), 14 (post, patient 9), 15 (post, patient 10). Lane 16 is a Coomassie blue stained PVDF membrane of the VRE extract Lane 17 contains molecular weight markers. Molecular weights of bands are as marked; and FIG. 3 shows sequential (lanes 1 and 2) IgM and sequential (lanes 3 and 4) IgG from a patient with a *S. aureus* septicaemia who recovered, blotted against the extract from the MRSA.

EXPERIMENTAL

Experiments below show the existence of immunodominant conserved antigens from Staphylococcus having molecular weights of 69 and 37 kDa. Patients who survived MRSA infection produced increased levels of antibody against these antigens whereas the non-survivors had no antibody against these antigens. In order to characterise the antigens, a genomic library was constructed for MRSA and screened for antigens recognised by the peritoneal dialysate and two clones isolated. Antibody from the peritoneal dialysate which bound to the expression product of the isolated clone s was separated from the expression product and bound to the 69 kDa MRSA antigen, showing that the same epitope was displayed by both the 69 kDa antigen and the isolated clone. The cloned MRSA DNA was then sequenced and putative amino acid sequences of two open reading frames (ORFs) derived and analysed. Analysis included comparison to sequence of the expression product derived by direct amino acid sequencing, comparison of the theoretical molecular weight to the observed expression product molecular weight and comparison to sequences of know proteins. This showed that two of the putative amino acid sequences (SEQ ED NOs: 10 and 11 and corresponding DNA sequence SEQ ID NO: 9) were possible expression products. Sequence comparison of these amino acid sequences on the BLAST and BEAUTY search facilities showed theem to be highly homologous to the IstA and IstB proteins respectively of *Bacillus thuringiensis* (Menou et al., 1990, J. of Bacteriology, 172: 6689–6696). Epitope mapping of SEQ ID NO: 10 (termed MRSA1) identified 3 epitopes (SEQ ID NOs: 12–14; MRSA1a, MRSA1b and MRSA1c respectively) and epitope mapping of SEQ ID NO: 11 (termed MRSA2) identified 1 epitope (SEQ ID NO: 15; termed MRSA2a). Antibody specific against the antigens was found to be protective in animal models and therefore the antigens and agents which neutralise their function are therapeutically useful. Similarly, binding agents which specifically bind to the antigens may be diagnostically useful. Immunogenic fragments of the antigens may be used in place of the antigens themselves for diagnosis and therapy.

Experiments below identify immunodominant conserved antigens of vancomycin resistant *Enteroccus faecium* (VRE) having molecular weights of 54 and 97 kDa. Patients who survive VRE infections produce increased levels of antibody against the antigens, whereas non-survivors have unchanged or decreased levels of antibody against the antigen over the course of their infection. In order to characterise the antigens, a genomic library was constructed for VRE and screened for antigen recognised by a peritoneal dialysate, and two clones isolated. Antibody from peritoneal dialysate which bound to the expression product of the isolated clone was separated from the expression product and bound to the 97 kDa VRE antigen, showing that the same epitope was displayed by both the 97 kDa antigen and the isolated clone. The cloned VRE DNA was then sequenced and putative amino acid sequences of the six open reading frames (ORFs) derived and analysed. Analysis included comparison to sequence of the expression product derived by direct amino acid sequencing, comparison of the theoretical molecular weight to the observed expression product molecular weight and comparison to sequences of know proteins. This showed that only one of the putative amino acid sequences (SEQ ID NO: 2; coded for by DNA sequence SEQ ID NO: 1) could correspond to the expression product. Sequence comparison of this on the BLAST and BEAUTY search facilities showed it to be highly homologous to known ABC transporter proteins, particularly to ATPase binding sites within ABC transporters. Epitope mapping of SEQ ID NO: 2 identified 1 generic and 5 specific epitopes (SEQ ID Nos: 3–8) which correspond to areas within the ABC transporter, particularly in and around ATP binding sites. Patient sera and dialysate which bound the 97 kDa and 54 kDa antigens and the epitopes was protective in an animal model, and thus agents which neutralise the function of ABC transporters of pathogens such as bacteria and fungi may be used for therapeutic purposes. Agents which detect specific ABC transporters may also be used diagnostically.

Immunoblotting

Antigen Preparation

Antigen was prepared by the following method. Using a clinical isolate of Vancomycin resistant enterococcus, an MRSA epidemic stain 16, an MRSA epidemic strain 2, the Oxford *S.aureus* and a clinical isolate of *S.epidermis,* 10 ml of brain heart infusion broth (Oxoid) was innoculated with the organism and grown up at 37° C. aerobically for 4 hours. This was added to 300 ml of the same broth and incubated on an orbital shaker at 37° C. for 24 hours. The culture was centrifuged at 2500 g for 15 minutes, resuspended in 10 ml of 10 mM Tris-HCl (pH 7.5) and repelleted as above. The organism was then fragmented in a hydraulic press (Enkoping, Sweden) at −20° C., centrifuged at 13000 rpm for 30 minutes, and the supernatant (containing antigen) stored at −20° C. Subsequently batches of antigen for the VRE and MRSA 16 were prepared by growing them at 30° C. and at 37° C. in the presence of 3 $\mu$g/ml Vancomycin.

Sera

The sera collected had been submitted to the bacteriology, virology and biochemistry laboratories for routine testing. It was stored at −20° C. until required for immunoblotting.

Patient Groups

Group 1 septicaemia patients had signs and symptoms (e.g. pyrexia) consistent with infection at a time when VRE was isolated from blood cultures. These patients were neutropenic during admission secondary to chemotherapy for haematological malignancies (mostly leukaemias). Neutropenia was defined as a neutrophil count of $<1.0\times10^9/1$. Pre- and post-infection serum were kept and tested in parallel. These were separated into survivors and non-survivors (those with positive blood cultures with a VRE who were unresponsive to chemotherapy and died).

In addition, peritoneal dialysate was available from a single patient with peritonitis due to a VRE.

Group 2 patients were considered to be colonized with VRE, in that at the time of isolation of these organisms the patients had no signs or symptoms of infection that could be attributed to VRE. This group was divided into Group 2a and Group 2b. Group 2a were patients all of whom would have been neutropenic at some point in their illnesses. Therefore, this subgroup will be referred to as colonized neutropenic patients. Group 2b patients were all renal or intensive care patients and none had been neutropenic. This subgroup will be referred to as colonized non-neutropenic patients. Post-colonization sera only was saved from Group 2 patients because colonization can be intermittent, and in any one patient it is never clear when exactly they first became colonized, or if perhaps they had been colonized during a previous admission.

Group 3 patients were the control group for the VRE study. The serum had been routinely collected from pregnant women from the community attending antenatal clinics. The level of VRE in the community is low at present, and the majority of women should not have encountered it. Hospitalised patients were not used as a control group because of the possibility of them having been unknowingly colonized with VRE.

Group 4 were patients with a septicaemia due to an MRSA, positive blood cultures who were treated with vancomycin therapy. Paired sera were available before and after the septicaemia. In addition, peritonea dialysate was available from a single patient with peritonitis due to an MRSA.

Group 5 were patients colonized with an MRSA who showed no clinical signs of infection.

Group 6 patients were the control group for the MRSA study. The serum had been routinely collected from pregnant women from the community attending antenatal clinics.

Group 7 were patients with a septicaemia due to an MSSA (methicillin sensitive *S.aureus*), positive blood cultures who were treated successfully. Paired sera were available before and after the septicaemia.

Preparation of the Polyacrylamide Gel

A 1.5 mm thick polyacrylamide gel was prepared in the vertical gel apparatus from a Protean II xi Cell (Biorad). A 10% resolving gel was poured first and left to polymerize at room temperature for 60 minutes. A ten lane comb was placed on top of this and the stacking gel poured round it and on top of the separating gel. This was left for 30 minutes to polymerize. The following were used to make the gels:

| Separating gel | |
|---|---|
| 30% acrylamide/0.8% bisacrylamide (Ultra pure Protogel, National diagnostics) | 25 ml |
| Separating gel buffer (see below) | 14.06 ml |
| 10% SDS | 0.75 ml |
| Distilled water | 35.2 ml |
| 10% ammonium persulphate | 350 μl |
| TEMED | 37.5 μl |
| Separating gel buffer | |
| Tris | 24.22 g |
| Distilled water | 40 ml |

Adjust the pH to 8.8 with concentrated HCl, then make up to 100 ml with distilled water.

| Stacking gel | |
|---|---|
| 30% acrylamide/0.8% bisacrylamide | 3.6 ml |
| Stacking gel buffer (see below) | 7.3 ml |
| 10% SDS | 0.3 ml |
| Distilled water | 19 ml |
| 10% ammonium persulphate | 300 μl |
| TEMED | 30 μl |
| Stacking gel buffer | |
| Tris | 6.05 g |
| Distilled water | 90 ml |

Adjust the pH to 6.8 with concentrated HCl.

Sample Preparation

The antigen to be run on the gel was solubilised by boiling with cracking buffer and distilled water. This was VRE and MRSA epidemic strain 16 grown at 37° C. for all sera. Five antibody positive sera forom VRE septicaemia cases were tested against VRE grown at 30° C. and at 37° C. in the presence of Vancomycin (3 μg/ml). Two antibody positive sera from MRSA septicaemia patients were immunoblotted against MRSA 2 and the Oxford *S.aureus*. Eight further sere were immunoblotted against the antigen derived from *S.epidermis* and the MRSA epidemic strain 16 grown at 30° C. and the USA epidemic strain 16 grown at 37° C. in the presence of Vancomycin (3 μg/ml). Multiples of the following were boiled as the amount of protein in this ratio was found to give good results on immunoblotting: supernatant (containing antigen), 15 μl; distilled water, 10 μl; cracking buffer, 25 μl.

| Cracking buffer. | |
|---|---|
| 20% SDS | 4 ml |
| Stacking buffer | 1 ml |
| Distilled water | 4 ml |
| 2-mercaptoethanol | 0.4 ml |
| Glycerol | 0.6 ml |

Bromophenol blue—a small amount added until the buffer is blue.

Each well was loaded with 50 μl of the above mixture. Rainbow coloured protein molecular weight markers (Amersham Life Science) were used on each gel in one lane. 20 μl of marker was boiled with 20 μl of cracking buffer before loading. The molecular weight markers were: myosin 220000, phosphorylase B 97400, bovine serum albumin 66000, ovalbumin 46000, carbonic anhydrase 30000, trypsin inhibitor 21500 and lysozyme 14300 (all molecular weights given in Daltons).

Gel Electrophoresis

Electrophoresis buffer was placed in the electrophoresis tank and in the cell above the gels. This formed the discontinous buffer system. Electrophoresis was carried out at a constant current of 40 mA per gel, with water cooling. It was run until the dye front had just run off the gel.

| Electrophoresis buffer | |
|---|---|
| Tris | 18.96 g |
| Glycine | 12 g |
| SDS | 3 g |
| Distilled water | 1 litre |

Transblotting

The gel was carefully removed from between the glass plates and the stacking gel removed. The separating gel was then placed onto nitrocellulose paper (Biorad) and this was enveloped between filter paper. The nitrocellulose and filter paper had been pre-soaked in transblotting buffer. This was placed in the transblotting tank (Hoefer) which contained transblotting buffer. The current was run at the maximum for 45 minutes and the system was water cooled. The nitrocellulose was removed and left to block overnight in 3% bovine serum albumin (BSA) at 4° C.

| Transblotting buffer | |
|---|---|
| Tris | 9.07 g |
| Glycine | 43.2 g |
| Methanol | 750 ml |
| Distilled water | 3 litre |
| Tris solution to make up 3% BSA | |
| Sodium chloride | 9 g |
| Tris | 1.2 g |
| Distilled water | 1 litre |

Antibody Probing and Staining

The nitrocellulose paper was cut into strips reflecting the wells and each placed in separate compartments in an incubation container. BSA solution (3%) was added to each strip and enough of the appropriate serum was added to this to give a 1:10 dilution. These were shaken at room temperature for 2 hours. The strips were then washed in washing solution for 30 minutes with the solution being changed every 6 minutes. Next a 1:1000 dilution in 3% BSA of anti-human immunoglobulin conjugated to alkaline phosphatase was added (Sigma). The main immunoblotting for serum from colonized or infected patients was for IgA, IgM and IgG. Hence this required three strips per serum, one incubated with anti-human IgA, one with anti-human IgM and one with anti-human IgG. The control group had one strip incubated with all three anti-human immunoglobulins at the same time. These were shaken for 1 hour at room temperature and the washing stage repeated. The substrate was prepared by adding 660 µl of nitro-blue tetrazolium solution and 330 µl of 5-bromo-4-chloro-3-indolyl phosphate solution to 100 ml of alternative alkaline phosphatase substrate buffer and 4 ml of this was added to each strip and shaken for 20 minutes. This was found to be the time taken for the strips to become sufficiently well stained.

| Washing solution | |
|---|---|
| Sodium chloride | 4.5 g |
| Tween 20 | 0.25 ml |
| Distilled water | 500 ml |
| Nitro-blue tetrazolium solution. | |
| Nitro-blue tetrazolium | 0.05 g |
| 70% N, N-dimethylformamide | 1 ml |
| 5-bromo-4-chloro-3-indolyl phosphate (BCIP) solution. | |
| BCIP | 0.05 g |
| 70% N, N-dimethylformamide | 1 ml |
| Alkaline phosphatase substrate buffer. | |
| Tris | 1.12 g |
| Sodium chloride | 0.58 g |
| Magnesium chloride | 0.1 g |
| Distilled water | 100 ml |

Adjust the pi to 9.5

Results

Vancomycin Resistant Enterococci

Immunoblotting (Tables 1 and 2; FIGS. 1 and 2) demonstrated multiple antigenic bands of which four were immunodominant (97, 57, 54 and 40 kDa). These antigens were conserved between isolates and present when the strains were grown with and without vancomycin. IgG was produced against the 97 kDa band in 11 out of the 12 patients who survived a septicaemia and it was present in 12 of the neutropenic patients who did not develop a septicaemia. IgM was produced in 8 and IgA in 4 of the septicaemia patients. In the case of the 54 kDa antigen, 10 patients with a septicaemia made an IgM response and 5 an IgA response. Four patients who were neutropenic and did not develop a septicaemia had an IgM response. A patient on chronic ambulatory peritoneal dialysis and infection in the fluid due to VRE had an IgM response to the 97 and 54 kDa bands in the serum and dialysate and no IgG response. The dialysate was used for screening the expression library (below).

TABLE 1

| Antigen | Colonized Group 2 | | | | | | Controls |
|---|---|---|---|---|---|---|---|
| apparent | neutropenic | | | non-neutropenic | | | Group 3 n = 60 |
| molecular | leukaemic n = 22 | | | renal n = 12 | | | combined IgM, |
| weight (kDa) | IgM | IgG | IgA | IgM | IgG | IgA | IgG and IgA |
| 97 | 4 | 12 | 0 | 1 | 0 | 2 | 3 |
| 57 | 1 | 2 | 0 | 0 | 1 | 0 | 7 |
| 54 | 4 | 3 | 1 | 1 | 0 | 0 | 4 |
| 40 | 0 | 4 | 0 | 1 | 1 | 0 | 1 |

TABLE 2

| Antigen | Group 1 Septicaemia (survived) n = 12 | | | | | | | | | Dead (n = 5) | | | | | |
|---|---|---|---|---|---|---|---|---|---|---|---|---|---|---|---|
| apparent | IgM | | | IgG | | | IgA | | | IgM | | igG | | IgA | |
| MW (kDa) | a | i | c | a | i | c | a | i | c | D | C | D | C | D | C |
| 97 | 8 | | | 11 | | 1 | 4 | 1 | | 1 | 1 | 1 | 1 | | 1 |
| 57 | 5 | | | 5 | 1 | 2 | 3 | 1 | | 2 | | | 2 | | |
| 54 | 10 | | | 2 | 1 | 5 | 5 | 1 | | 2 | | 1 | 1 | | |
| 40 | 4 | 1 | | 4 | 1 | | | | | 2 | | | 2 | | | a = appeared, in paired sera, from nil
i = increased, in paired sera at least doubling of intensity
c = constant
d = decreased, in paired sera at least a halving of intensity Conclusions The 97 and 54 kDa enterococcal antigens are immunodominant and may be used therapeutically and diagnostically. Further immunoblotting demonstrated the presence of the antigens when the VRE was grown at 30° C. and in the presence of Vancomycin at 37°.

Methicillin Resistant *S. aureus*

Immunoblotting (Table 3; FIG. 3) sera revealed antigens of apparent molecular weight 31–120 kDa. The most immunodominant bands were at 69 and 37 kDa. In the septicaemia group there was an increased IgM or IgG in 3 out of the 5 patients against the 69 kDa band. Respectively the numbers for the 37 kDa band were 4 for IgM and 3 for IgG. These antibodies were absent in the patient who died but present in some of the patients who were colonized and did not develop infection. They were also present in low numbers in the control sera from the pregnant women. The peritoneal dialysate reacted with the 37 kDa band (IgG) and the 69 kDa band (IgM and IgG) and was used for screening the expression library (below).

had a higher vancomycin level (30 μg/ml) than patient 1 (12 μg/ml). 20 CD-1 mice were given $1 \times 10^7$ of the MRSA epidemic strain '16' intravenously and 2 hours later two groups of 10 mice were each given 100 ml of the serum from either patient 1 or 2 as a single intravenous volume.

TABLE 3

| Antigen apparent mw (kDa) | Group 4 Septicaemia survived (n = 5) | | | | Group 5 septicaemia died (n = 1) | | Group 5 colonized (n = 3) | | Group 6 Control (n = 10) | | Group 7 MSSA septicaemia survived (n = 3) | | | |
|---|---|---|---|---|---|---|---|---|---|---|---|---|---|---|
| | IgM i | IgM c | IgG i | IgG c | IgM | IgG | IgM | IgG | IgM | IgG | IgM i | IgM c | IgG i | IgG c |
| 120 | 0 | 3 | 0 | 3 | 1 | 1 | 1 | 1 | 2 | 1 | 0 | 3 | 0 | 3 |
| 84 | 1 | 2 | 0 | 3 | 0 | 0 | 1 | 1 | 2 | 2 | 0 | 0 | 0 | 0 |
| 69 | 2 | 2 | 1 | 3 | 0 | 0 | 2 | 2 | 2 | 1 | 1 | 0 | 1 | 0 |
| 67 | 2 | 2 | 0 | 4 | 1 | 1 | 0 | 0 | 1 | 3 | 0 | 0 | 0 | 0 |
| 60 | 0 | 2 | 0 | 3 | 0 | 0 | 1 | 1 | 3 | 1 | 0 | 0 | 0 | 0 |
| 53 | 0 | 4 | 0 | 3 | 0 | 0 | 0 | 1 | 2 | 2 | 0 | 0 | 0 | 0 |
| 42 | 0 | 1 | 1 | 2 | 1 | 0 | 1 | 0 | 1 | 2 | 0 | 0 | 0 | 0 |
| 37 | 4 | 0 | 3 | 2 | 0 | 0 | 2 | 3 | 2 | 2 | 2 | 0 | 2 | 0 |
| 33 | 3 | 1 | 2 | 3 | 0 | 1 | 1 | 0 | 1 | 1 | 0 | 0 | 0 | 0 |
| 31 | 2 | 1 | 2 | 1 | 0 | 0 | 1 | 0 | 1 | 1 | 0 | 0 | 0 | 0 | i = increased
c = constant

Conclusions

Patients seroconvert to the 37 kDa antigen if they recover and also display immunogenicity to the 69 kDa antigen. Hence the 37 and 69 kDa antigens may be used therapeutically aid diagnostically. Equivalent bands at 120, 84, 69, 53 and 37 kDa were also demonstrated by immunoblotting in MRSA strain 2 and the Oxford *S.aureus* and at 120, 69 and 37 kDa in the *S.epidermidis*.

Antibody Therapy VRE

In order to test the therapeutic potential of antibody specific to the *E.faecium* antigens, 10 control mice were injected with 200 μl of saline solution and 10 test mice were injected with 200 μl of antibody serum from a patient who had recovered from a septicaemia 1 hour later the mice were each injected with 100 μl of $5 \times 10^8$ colony forming units (CFU) of vancomycin resistant *E. faecium*.

Of the 10 control mice, 8 died whilst only 4 of the test mice died, indicating that antibody specific to the immunodominant enterococcal antigens may be used therapeutically.

VRE

Two sets of 30 female CD-1 mice weighing 22 g each were infected via the tail vein with $3 \times 10^9 / 100$ μl bolus of a vancomycin resistant *E.faecium*. Infected mice were subsequently injected with either (Group A) 200 μl of peritoneal dialysate fluid (as previously described) from a patient with CAPD peritonitis due to VRE, or with (Group B) 200 μl of normal fluid.

At 48 hours 5 out of 30 died in Group A as against 9 out of 30 in Group B.

MRSA

Serum was obtained from two patients. Patient 1 had recovered from a subphrenic abscess which was treated by vancomycin. Patient 1 serum antibody was positive for both the 37 and 69 kDa antigens. Patient 2 was treated for an MRSA septicaemia with vancomycin. The patient 2 serum antibody was early preimmune and negative for the 37 and 69 kDa antigens. Vancomycin assays showed that patient 2

Results (Table 4) show that serum antibody positive for both the 37 and 69 kDa antigens was protective against MRSA, with a mortality rate of 20% in the group treated with patient 1 (antibody positive for both the 37 and 69 kDa antigens) as compared to a mortality rate of 50% for the other group.

TABLE 4

| Time | Patient 1 | Patient 2 |
|---|---|---|
| Day 1 | All Well | All Well |
| Days 2–6 | All Well | 1 death |
| Day 7 | 2 deaths (20% mortality) | 4 more deaths (50% mortality) |

Preparation and Screening of Genomic Expression Libraries of Vancomycin Resistant Enterococcus and Methicillin Resistant *Staphlyococcus aureus*

A genomic library (one for each of vancomycin resistant *Enterococcus faecium* and multiply resistant *Staphylococcus aureus*) was constructed in the expression/cloning vector lambda ZAP express, essentially as described by Young and Davies (1983, PNAS USA, 80: 1194–1198). Chromosomal DNA from a clinical isolate was partially digested by Sau3a and fragments in the size range of 2 to 9 kbp were inserted into the vector, resulting in the production of β galactosidase fusion proteins. Each library was screened with antibody positive (37 and 69 kDa bands for MRSA or 54 and 97 kDa bands for VRE) peritoneal dialysate fluids (1 in 100 dilution) from patients with the respective infection. Positive clones were detected using alkaline phosphatase conjugated goat anti-human immuglobulin (IgG) (1 in 5,000) (Sigma, Poole UK). Lysogens were prepared from positive clones in *Escherichia coli* Y1089 according to Huynh, Young and Davies (1985, DNA cloning vol 1, a practical approach, IRL Press Oxford, p 49–78, Ed. D. M. Glover). The β galactosidase fusion proteins were detected by immunoblotting using respective peritoneal dialysate fluid (1 in 10) and a monoclonal antibody to β galactosidase (1 in 1,000). The epitope expressed by each of the positive clones was identified by antigen-selection as descried by Lyon et al. (1986, PNAS USA, 83: 2989–2993). For this, the peritoneal dialysate fluid was affinity purified by hybridising with positive recombinant lambda plaques. The bound antibody was then eluted with glycine buffer pH 2.8, and used to immunoblot lysates of the relevant bacteria.

DNA Sequencing

PCR with T3 and T7 forward and reverse primers was used to amplify insert DNA from sera positive clones. This was subcloned into the TA Cloning System (version 1.3, Invitrogen Corporation, Oxon, UK) prior to DNA sequencing using the dideoxy termination method (sequence version 2.0 kit; United States Biochemical, Cambridge, UK). Initial sequencing reactions were performed using sequencing universal primers, the remaining sequence being determined using a primer walking strategy by progressively synthesising sequencing primers to generate new sequence data.

Epitope Mapping

A series of overlapping nonapeptides covering the derived amino acid sequence were synthesised on polyethylene pins with reagents from an epitope scanning kit (Cambridge Research Biochemicals, Cambridge, UK) as described previously by Geysen et al. (1987, Journal of Immunological Methods, 102: 259–274). Peptide 1 consisted of residues 1 to 9, peptide 2 consisted of residues 2 to 10 etc. This was performed for the ABC transporter protein derived from the VRE (FIG. 1) and MRSA1 and MRSA2 from the MRSA clone. The reactivity of each peptide with patient sera (diluted 1 in 2000) was determined for IgG by ELISA. Data were expressed as A405 after 30 min of incubation. Sera were antibody positive, 54 and 97 kDa from patients who had recovered from a VRE septicaemia (n=6) and the control was a serum sample from a patient who subsequently died from a septicaemia caused by a VRE (n=1). For MRSA1 and MRSA2, sera was mapped from patients who had recovered from the infection (n=3) and the control was from a patient who had died (n=1).

Results

MRSA

Four positive clones were detected with the dialysate from the patient. Two of these produced a fusion protein of 180 kDa which reacted with the peritoneal dialysate and a monoclonal antibody specific for β galactosidase. Antigen selection demonstrated an epitope expressed by both clones tested which reacted with the 69 kDa antigen of MRSA epidemic strain 16. Sequencing demonstrated that there were 2 ORFs which were homologous to the IstA and IstB proteins expressed by the IS232 insertion sequence of Bacillus thuringiensis (Menou et al., 1990, J. of Bacteriology, 172:6689–6696).

VRE

Four positive clones were detected with the patient dialysate. Two of these produced a fusion protein of 140 kDa which reacted with both the peritoneal dialysate and the monoclonal antibody against β galactosidase. Antigen selection demonstrated an epitope for two of the clones which reacted with the 97 kDa antigen of the VRE strain.

Sequencing demonstrated a partial sequence in frame with the β galactosidase gene. The total insert size was 4.5. kb. The derived amino acid sequence produced a protein with two ATP- binding domains and a sequence homologous to the group of proteins which are ABC transporters (Fath and Kolter, 1993, Microbiological Reviews, 57: 995–1017).

Epitope Maping

This showed 5 epitopes as derived by three or more consecutive wells with a mean optical density at least two standard deviations above the results for the serum from the control patient. For VRE these were SEQ ID NOs: 3–8; for MRSA1 these were SEQ ID NOs: 12–14; and for MRSA2 SEQ ID NO: 15.

What is claimed is:

1. A method of treatment of a human or animal patient having a bacterial infection, comprising treating said patient with an antibody or antibody binding fragment specific to an immunogenic fragment of an ABC transporter protein of said bacterium such that said bacterial infection is treated, wherein the bacterium is *E. faecium* and the immunogenic fragment has the sequence of SEQ ID NO : 6, 7 or 8, and said antibody or antibody binding fragment binds to at least one sequence of SEQ ID NO 6, 7 or 8.

2. The method of claim 1 wherein said immunogenic fragment has the sequence of SEQ ID NO 6.

3. The method of claim 1 wherein said immunogenic fragment has the sequence of SEQ ID NO 7.

4. The method of claim 1 wherein said immunogenic fragment has the sequence of SEQ NO 8.

5. The method of claim 1 wherein said antibody or said antibody binding fragment binds to SEQ ID NO 6.

6. The method of claim 1 wherein said antibody or said antibody binding fragment binds to SEQ ID NO 7.

7. The method of claim 1 wherein said antibody or said antibody binding fragment binds to SEQ ID NO 8.

8. The method of claim 2 wherein said antibody or said antibody binding fragment binds to SEQ ID NO 6.

9. The method of claim 3 wherein said antibody or said antibody binding fragment binds to SEQ ID NO 7.

10. The method of claim 4 wherein said antibody or said antibody binding fragment binds to SEQ ID NO 8.

* * * * *

SEQUENCE LISTING

<160> NUMBER OF SEQ ID NOS: 15

<210> SEQ ID NO 1
<211> LENGTH: 540
<212> TYPE: DNA
<213> ORGANISM: Enterococcus faecium

<400> SEQUENCE: 1

```
atggtggatt ggttatggac atccgttttg aacagtagat tcacttatca gccgaataca        60
ccatttgaac aaagagcctt atttgacatc aataagaaga tcaaaggaaa cagttatact       120
gcattagtag ggcataccgg aagcgggaaa tcaaccttac ttcagcattt gaatgcgctt       180
gttaagccaa caagcggtac agtccatatt ggagaacgag atattcagcc ggatacggat       240
aataagaatt taaagcccat ccgaaaaaaa gttggcatcg tctttcagtt tccagaagca       300
cagctattcg aagaaacggt agcaaaagac attgctttcg gtcctaaaaa ctttggtgtc       360
agcgaagaag aagcactagt cctagcaaaa gaaacattag aacaagttgg gctggatgaa       420
agctatttgg aacgttcgcc atttgaactt tcaggagggc aaatgcgtag agtagcaatc       480
gctggtgtgc ttgccatgag gccggaagta cttgtattgg atgaaccaac ggcaggactt       540
```

<210> SEQ ID NO 2
<211> LENGTH: 180

```
<212> TYPE: PRT
<213> ORGANISM: Enterococcus faecium

<400> SEQUENCE: 2

Met Val Asp Trp Leu Trp Thr Ser Val Leu Asn Ser Arg Phe Thr Tyr
  1               5                  10                  15

Gln Pro Asn Thr Pro Phe Glu Gln Arg Ala Leu Phe Asp Ile Asn Lys
             20                  25                  30

Lys Ile Lys Gly Asn Ser Tyr Thr Ala Leu Val Gly His Thr Gly Ser
         35                  40                  45

Gly Lys Ser Thr Leu Leu Gln His Leu Asn Ala Leu Val Lys Pro Thr
 50                  55                  60

Ser Gly Thr Val His Ile Gly Glu Arg Asp Ile Gln Pro Asp Thr Asp
 65                  70                  75                  80

Asn Lys Asn Leu Lys Pro Ile Arg Lys Lys Val Gly Ile Val Phe Gln
                 85                  90                  95

Phe Pro Glu Ala Gln Leu Phe Glu Thr Val Ala Lys Asp Ile Ala
            100                 105                 110

Phe Gly Pro Lys Asn Phe Gly Val Ser Glu Glu Ala Leu Val Leu
            115                 120                 125

Ala Lys Glu Thr Leu Glu Gln Val Gly Leu Asp Glu Ser Tyr Leu Glu
130                 135                 140

Arg Ser Pro Phe Glu Leu Ser Gly Gly Gln Met Arg Arg Val Ala Ile
145                 150                 155                 160

Ala Gly Val Leu Ala Met Arg Pro Glu Val Leu Val Leu Asp Glu Pro
                165                 170                 175

Thr Ala Gly Leu
            180

<210> SEQ ID NO 3
<211> LENGTH: 7
<212> TYPE: PRT
<213> ORGANISM: Enterococcus sp.
<220> FEATURE:
<221> NAME/KEY: UNSURE
<222> LOCATION: (1)
<223> OTHER INFORMATION: Generic epitope - any amino acid
<220> FEATURE:
<221> NAME/KEY: UNSURE
<222> LOCATION: (3)
<223> OTHER INFORMATION: Generic epitope - any amino acid

<400> SEQUENCE: 3

Xaa Gly Xaa Gly Lys Ser Thr
  1               5

<210> SEQ ID NO 4
<211> LENGTH: 7
<212> TYPE: PRT
<213> ORGANISM: Enterococcus faecium

<400> SEQUENCE: 4

Thr Gly Ser Gly Lys Ser Thr
  1               5

<210> SEQ ID NO 5
<211> LENGTH: 7
<212> TYPE: PRT
<213> ORGANISM: Enterococcus faecium

<400> SEQUENCE: 5
```

```
Leu Leu Gln His Leu Asn Ala
 1               5
```

<210> SEQ ID NO 6
<211> LENGTH: 5
<212> TYPE: PRT
<213> ORGANISM: Enterococcus faecium

<400> SEQUENCE: 6

```
Lys Val Gly Ile Val
 1               5
```

<210> SEQ ID NO 7
<211> LENGTH: 6
<212> TYPE: PRT
<213> ORGANISM: Enterococcus faecium

<400> SEQUENCE: 7

```
Phe Gly Pro Lys Asn Phe
 1               5
```

<210> SEQ ID NO 8
<211> LENGTH: 8
<212> TYPE: PRT
<213> ORGANISM: Enterococcus faecium

<400> SEQUENCE: 8

```
Arg Val Ala Ile Ala Gly Val Leu
 1               5
```

<210> SEQ ID NO 9
<211> LENGTH: 1457
<212> TYPE: DNA
<213> ORGANISM: Staphylococcus aureus

<400> SEQUENCE: 9

```
atttaaagaa attattaata aaaaaattga attaggatgt acagctatgg ccattttttaa      60
atatatagag aaaaagggtt atgaaggtaa atatactatt ctacgagaat actgtaaaaa     120
taaaaaacaa aatgagacta aaaaagcaac tatacgcgta gaaactaatc ccggtatagc     180
tgctcaagta gactggaaag aagatatggt aatgcatgat aagtttggca gaacttatca     240
attcaacatc tttctttacg ttctacacta ttcaaaaatg aagtatatca cattaacttg     300
ggatagaaaa caagataccT tatttgaatg tttaaaagac gcttttgaat acaccgaagg     360
ggttccaaaa gaaatctggt tcgataatat gagaactgta gttgatcgac ctagaacaca     420
atataaaaaa gtcgtcttta ataatttatt ttatcaattt agtaaggatg ccaactttga     480
acctattgct tgtagaccct atcgtcctca acaaaaggg tctgttgaat cattagctaa      540
atttgttgaa cagcgtttaa gaccatacga ttatgaattt tatgatgctg tagaacttat     600
tgggctagta aacgatttat gtcacgaatt gaatcactta gaaatttcac aagcaacaga     660
acaacgacct atcgacgttt tcaattatga agaaaagaa catttaaatt cttttaatgc     720
caagttacta gatacttaca tcgaaaatga gtgtataaga atcgtttcta agaatcgat      780
gattaacttt agaaaaggta aatactcggt acctactaaa tacattggtg aagaagtaca     840
agtgatattc aataattcta ctgatgaatt gctgatttat tatgatggtg aattaataag     900
acggcataat ctatccgaaa gaaaatttaa ttatatcgtt gaagatatga gtgaaatatt     960
aaaatcagat gtatttaaac ataaggatga caaagaaatt cttacgtata tagaaaattc    1020
attattactg tatgacgaaa tttaggagga ctttcgatga atacgaacca tcaaaaatta    1080
```

-continued

```
cttaataact ttgaaatatt aaaactaaaa aaattcaaag attattatcc aaactatatt    1140
gaattacttt ctaaaaatga gaaatcttta actgaaatat tgattgattt aacggaaaaa    1200
gaaatagaat atcaatcaga attaaaattt aaacgtgctg tgaattcagc acgtttccct    1260
aaaataaaat atttacatga ttttgatttc atgtttcaac ctaagtataa atcaacaaga    1320
aatactcact ttaaaatcta tgcattttt agaagatagt ataaatattt gtttctagta    1380
atagtggtgt tggtaaaaca cacctagcaa tctcattagg aatagaggca tgttagcaaa    1440
atataaagac tagatcc                                                   1457
```

<210> SEQ ID NO 10
<211> LENGTH: 347
<212> TYPE: PRT
<213> ORGANISM: Staphylococcus aureus

<400> SEQUENCE: 10

```
Phe Lys Glu Ile Ile Asn Lys Lys Ile Glu Leu Gly Cys Thr Ala Met
  1               5                  10                  15

Ala Ile Phe Lys Tyr Ile Glu Lys Lys Gly Tyr Glu Gly Lys Tyr Thr
             20                  25                  30

Ile Leu Arg Glu Tyr Cys Lys Asn Lys Gln Asn Glu Thr Lys Lys
         35                  40                  45

Ala Thr Ile Arg Val Glu Thr Asn Pro Gly Ile Ala Ala Gln Val Asp
     50                  55                  60

Trp Lys Glu Asp Met Val Met His Asp Lys Phe Gly Arg Thr Tyr Gln
 65                  70                  75                  80

Phe Asn Ile Phe Leu Tyr Val Leu His Tyr Ser Lys Met Lys Tyr Ile
                 85                  90                  95

Thr Leu Thr Trp Asp Arg Lys Gln Asp Thr Leu Phe Glu Cys Leu Lys
            100                 105                 110

Asp Ala Phe Glu Tyr Thr Glu Gly Val Pro Lys Glu Ile Trp Phe Asp
        115                 120                 125

Asn Met Arg Thr Val Val Asp Arg Pro Arg Thr Gln Tyr Lys Lys Val
    130                 135                 140

Val Phe Asn Asn Leu Phe Tyr Gln Phe Ser Lys Asp Ala Asn Phe Glu
145                 150                 155                 160

Pro Ile Ala Cys Arg Pro Tyr Arg Pro Gln Thr Lys Gly Ser Val Glu
                165                 170                 175

Ser Leu Ala Lys Phe Val Glu Gln Arg Leu Arg Pro Tyr Asp Tyr Glu
            180                 185                 190

Phe Tyr Asp Ala Val Glu Leu Ile Gly Leu Val Asn Asp Leu Cys His
        195                 200                 205

Glu Leu Asn His Leu Glu Ile Ser Gln Ala Thr Glu Gln Arg Pro Ile
    210                 215                 220

Asp Val Phe Asn Tyr Glu Glu Lys Glu His Leu Asn Ser Phe Asn Ala
225                 230                 235                 240

Lys Leu Leu Asp Thr Tyr Ile Glu Asn Glu Cys Ile Arg Ile Val Ser
                245                 250                 255

Lys Glu Ser Met Ile Asn Phe Arg Lys Gly Lys Tyr Ser Val Pro Thr
            260                 265                 270

Lys Tyr Ile Gly Glu Glu Val Gln Val Ile Phe Asn Asn Ser Thr Asp
        275                 280                 285

Glu Leu Leu Ile Tyr Tyr Asp Gly Glu Leu Ile Arg Arg His Asn Leu
    290                 295                 300
```

```
Ser Glu Arg Lys Phe Asn Tyr Ile Val Glu Asp Met Ser Glu Ile Leu
305                 310                 315                 320

Lys Ser Asp Val Phe Lys His Lys Asp Asp Lys Glu Ile Leu Thr Tyr
                325                 330                 335

Ile Glu Asn Ser Leu Leu Leu Tyr Asp Glu Ile
                340                 345

<210> SEQ ID NO 11
<211> LENGTH: 100
<212> TYPE: PRT
<213> ORGANISM: Staphylococcus aureus

<400> SEQUENCE: 11

Met Asn Thr Asn His Gln Lys Leu Leu Asn Asn Phe Glu Ile Leu Lys
1               5                   10                  15

Leu Lys Lys Phe Lys Asp Tyr Tyr Pro Asn Tyr Ile Glu Leu Leu Ser
                20                  25                  30

Lys Asn Glu Lys Ser Leu Thr Glu Ile Leu Ile Asp Leu Thr Glu Lys
            35                  40                  45

Glu Ile Glu Tyr Gln Ser Glu Leu Lys Phe Lys Arg Ala Val Asn Ser
50                  55                  60

Ala Arg Phe Pro Lys Ile Lys Tyr Leu His Asp Phe Asp Phe Met Phe
65                  70                  75                  80

Gln Pro Lys Tyr Lys Ser Thr Arg Asn Thr His Phe Lys Ile Tyr Ala
                85                  90                  95

Phe Phe Arg Arg
            100

<210> SEQ ID NO 12
<211> LENGTH: 7
<212> TYPE: PRT
<213> ORGANISM: Staphylococcus aureus

<400> SEQUENCE: 12

Ala Gln Val Asp Trp Lys Glu
1               5

<210> SEQ ID NO 13
<211> LENGTH: 10
<212> TYPE: PRT
<213> ORGANISM: Staphylococcus aureus

<400> SEQUENCE: 13

Ala Phe Glu Tyr Thr Glu Gly Val Pro Lys
1               5                   10

<210> SEQ ID NO 14
<211> LENGTH: 6
<212> TYPE: PRT
<213> ORGANISM: Staphylococcus aureus

<400> SEQUENCE: 14

Thr Lys Ser Gly Val Glu
1               5

<210> SEQ ID NO 15
<211> LENGTH: 9
<212> TYPE: PRT
<213> ORGANISM: Staphylococcus aureus

<400> SEQUENCE: 15
```

```
Ser Gly Val Gly Lys Thr His Leu Ala
  1               5
```